(12) United States Patent
Watkins

(10) Patent No.: US 6,348,942 B1
(45) Date of Patent: Feb. 19, 2002

(54) ENHANCED UNDERWATER VISIBILITY

(75) Inventor: Wendell R. Watkins, El Paso, TX (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/197,539

(22) Filed: Nov. 9, 1998

Related U.S. Application Data

(60) Provisional application No. 60/077,572, filed on Mar. 6, 1998.

(51) Int. Cl.[7] .................................................. H04N 7/18
(52) U.S. Cl. ........................... 348/81; 348/122; 348/48; 348/31; 348/117
(58) Field of Search ............................ 348/31, 48, 117, 348/122, 123, 81; H04N 7/18

(56) References Cited

U.S. PATENT DOCUMENTS

| | | | |
|---|---|---|---|
| 4,707,128 A | 11/1987 | Coles | 356/5.04 |
| 5,140,463 A | 8/1992 | Yoo et al. | 359/559 |
| 5,313,261 A | 5/1994 | Leatham et al. | 356/5.04 |
| 5,371,368 A | 12/1994 | Alfano et al. | 250/358.1 |
| 5,467,122 A | 11/1995 | Bowker et al. | 348/31 |
| 5,625,458 A | 4/1997 | Alfano et al. | 356/446 |

*Primary Examiner*—Nhon T Diep
(74) *Attorney, Agent, or Firm*—Paul S. Clohan, Jr.; William Randolph

(57) ABSTRACT

A system for enhancing underwater visibility is described that uses left and right alternately chopped laser illumination, filtered wide baseline stereo imaging and specular reflectors for deblurring the images. Two stereo images are compared to determine the pattern of backscattered light and the resultant backscatter pattern is subtracted from the images. Inverse point spread filtering based on the fusion of the specular reflector pattern is next performed to further improve the images, and stereoscopic is display for enhanced visibility in turbid and murky mediums. The invention has broad application for underwater exploration and search and recovery operations, and is especially useful for detection and removal of underwater mine hazards.

19 Claims, 4 Drawing Sheets

FORWARD LOOKING STEREO IMAGES CORRECTED FOR BACKSCATTER AND DEBLURRED USING RESULTS FROM BACKWARD IMAGERY

BACKWARD LOOKING STEREO IMAGES CORRECTED FOR BACKSCATTER AND DEBLURRED USING SPECULAR REFLECTING SPHERES

OVERLAID BACKWARD AND FORWARD LOOKING IMAGERY CORRECTED FOR BACKSCATTER AND BLURRING FROM WHICH THE RANGE TO MINE (M) CAN BE DELIVERED

ENHANCED UNDERWATER VISIBILITY

CROSS-REFERENCE TO RELATED APPLICATIONS

This appln claims benefit of Prov. No. 60/077,572 filed Mar. 6, 1998.

The present application is related to copending U.S. patent application Ser. No. 08/986,988 filed Dec. 11, 1997 entitled "Method and Apparatus for Increased Visibility through Fog and Other Aerosols," incorporated herein by reference as if fully set forth, hereinafter referred to as the "copending patent application."

STATEMENT REGARDING FEDERALLY SPONSORED RESEARCH OR DEVELOPMENT

Not Applicable.

BACKGROUND OF THE INVENTION

Murky, turbid, water causes serious problems for underwater navigation and exploration, especially in the area of detection and removal of underwater mine hazards. In this case, it basically costs one mine detection system per mine hazard because the detection process itself detonates the mine and destroys the nearby sensor. However, if a mine could be pinpointed visually from a safe distance in murky or turbid water, it could be detonated or safely avoided without destroying the sensor. Thus, there is a need for a system that can enhance underwater visibility in turbid or murky waters or in highly scattering media, generally. In addition, the location and recovery of submerged wreckage is frequently hampered by turbid water. A system to enhance visibility in murky, turbid waters could be extremely useful in such recovery operations.

BRIEF SUMMARY OF THE INVENTION

It is therefore an object of the present invention to provide a method for improving and enhancing visibility and object detection in turbid and murky water and other fluid mediums. It is also an object of the invention to provide an underwater visibility enhancement system for underwater exploration and search and rescue missions where turbid, murky, water impedes the rapid location and identification of submerged vessels and the like.

These and other objects are achieved by a system that uses an active hyperstereo imaging system to provide an observer with an improved and enhanced stereo image of the objects submersed in turbid or murky water. A matched pair of illuminating lasers and imaging cameras are alternately chopped. The left stereo camera is illuminated from the right laser and the right stereo camera is illuminated from the left laser. This produces opposite side-to-side backscatter radiation gradients from the scattering media. Specular reflection from objects and surfaces will not have this gradient so that appropriate signal processing techniques can be used to eliminate the backscatter and deblur scene content.

Another aspect of the invention of this application is to provide lasers for illumination that are optimum for looking through water. Lasers emitting light at around 532 nm or blue-green are best suited to this purpose. Another aspect of the invention of this application involves positioning specular reflectors behind the vessel since it is not practical to position specular reflectors in the forward direction. Accordingly, the vessel drags a tether behind it with a set of specular reflecting spheres. The spheres are spaced apart so as to provide sufficient spatial information to perform hyperstereo fusion and inverse filtering to minimize point spread blurring.

Another aspect of the invention of this application involves providing an illumination and camera system to utilize the aft specular reflecting spheres for deblurring. Accordingly, there are simultaneous forward and backward laser and camera pairs which are alternately chopped. Thus, an embodiment of the present application provides four instrumentation pods, each with matched lasers and cameras. Lasers in the two instrumentation pods on the same side of the vessel illuminate forward and backward while matched cameras on the other side collect both forward and backward imagery from the opposite side. The other two lasers are blocked initially and then illuminate forward and backward from the opposite side of the vessel while a second pair of matched cameras on the side of the vessel where the lasers were initially illuminating are now blocked.

In accordance with another aspect of the invention, the set of imagery from the backward looking stereo cameras is processed to reduce backscattering by using the side-to-side scattering intensity gradient caused by the off-axis illuminating lasers followed by appropriate inverse filtering to eliminate point spread function blurring. The forward looking stereo imagery has the same method for the reduction of backscatter performed followed by the deblurring inverse point spread function derived from the backward looking cameras.

Finally, in a preferred embodiment, the resultant stereo imagery is viewed by merging the two sets of stereo imagery. First, a set of backward looking image fields or frames are displayed and then a set of forward looking image fields or frames are displayed. The reference specular reflecting spheres are superimposed on the forward looking wide baseline stereo imagery. This allows the observer to maintain stereo fusion even when there are no objects, such as underwater mines, in the forward looking field of view. When there is an object such as an underwater mine in the forward looking field of view, the distance to the mine can be estimated using the stereo depth perception and determining where the mine falls in the reference grid formed by the linear array of specular reflecting spheres from the backward looking cameras which are overlaid on the forward looking imagery.

In accordance with another aspect of the invention, a pulsed laser may be used instead of a continuous wave laser is used and the opposite side cameras may be left blocked during the first few nanoseconds after the laser pulse to reduce the magnitude of the backscattered radiation from the murky water close to the vessel.

Still other objects and advantages of the present invention will become readily apparent to those skilled in this art from the detailed description, wherein only preferred embodiments of the present invention are shown and described, simply by way of illustration of the best mode contemplated of carrying out the present invention. As will be realized, the present invention is capable of other and different embodiments, and its several details are capable of modifications in various obvious respects, all without departing from the present invention. Accordingly, the drawings and descriptions are to be regarded as illustrative in nature, and not as restrictive.

DETAILED DESCRIPTION OF THE INVENTION

One of the key elements of this invention is the enhanced contrast obtained when low contrast scenes are viewed using wide baseline stereo goggle displays. This arises because of the strong physical process human vision utilizes to fuse the two stereo images for depth perception. In my copending patent application, I explain how hyperstereo vision (i.e., stereo baseline imagery with baseline separations much larger than the human eye spacing) can be used to see through fog for landing aircraft at airports or on aircraft carriers. Those concepts, with some important modifications, can be used to the same advantage in penetrating murky and turbid water.

Typically, what happens when one attempts to look through turbid water is that the backscatter from the suspended particulate matter is so intense that there is not enough contrast left to distinguish larger objects. What is needed is a method to illuminate the objects with radiation that can be used to derive what the objects look like through the backscatter. In general, radio and radar and other relatively long wave electromagnetic radiation through the infrared range does not penetrate well through water and other liquids. In addition, spatial resolution degrades as wavelength increases. Use of the thermal or infrared radiation is not a practical option because it does not effectively penetrate in water. Midband visible light, however, penetrates reasonably well and provides adequate spatial resolution. In particular, blue-green light is optimal for looking through water.

Figure 1:
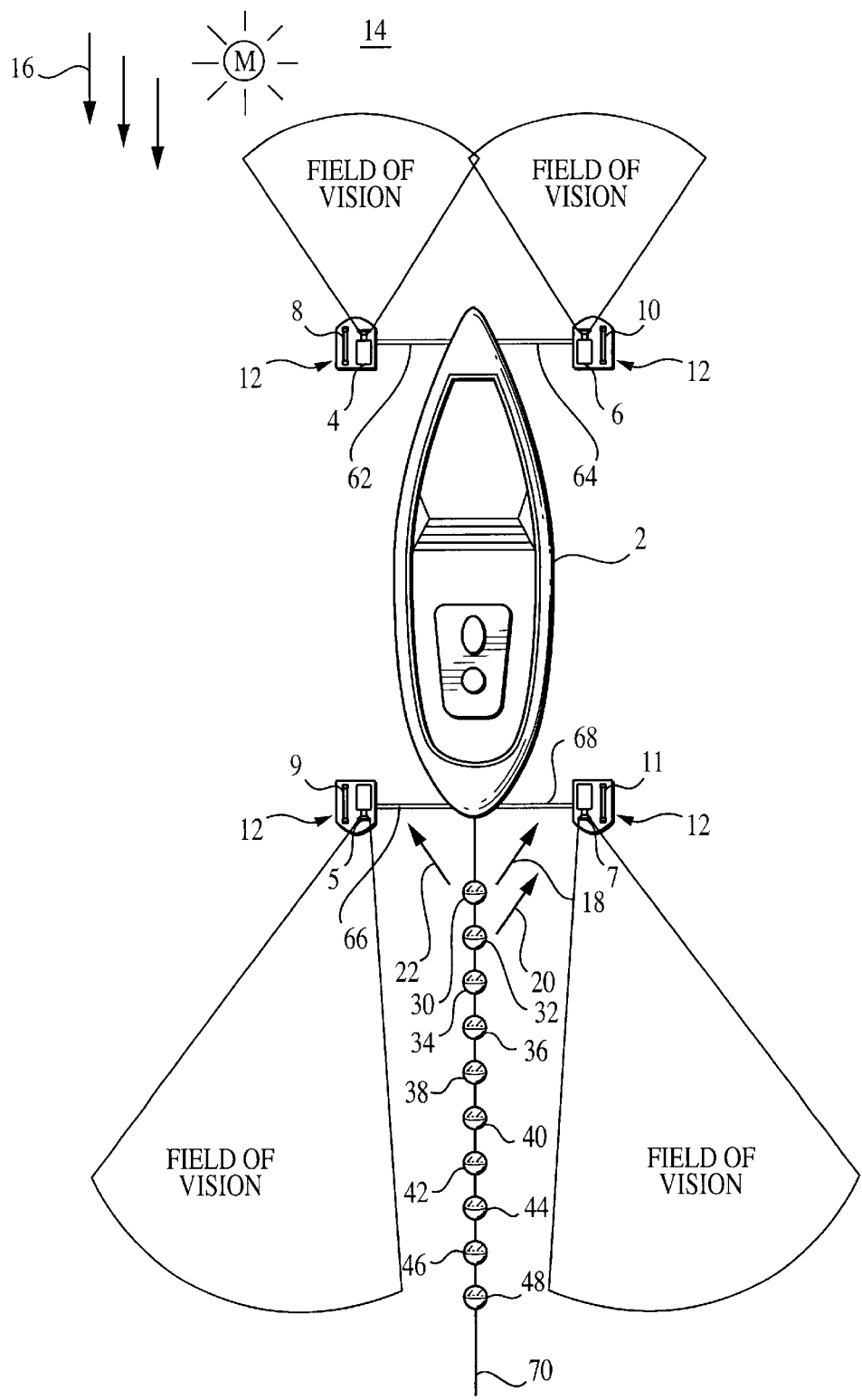
FIG. 1 depicts the use of chopped lasers, filtered cameras, specular reflectors and hyperstereo vision for enhancing underwater visibility from a surface ship.

The basic concept of the invention for seeing through turbid, murky water is straight forward and is depicted in FIG. 1. One laser 8 and one camera 4 are mounted on the left side (port) of the vessel 2 looking or pointed forward. Another laser 10 and another camera 6 are mounted on the right (starboard) side looking forward. These units are mounted symmetrically about the keel of the vessel.

Another laser 9 and camera 5 are mounted on the left side (port) of the vessel 2 looking or pointed backward. Still another laser 11 and another camera 7 are mounted on the right (starboard) side looking backward. Cameras 4, 5, 6, and 7 each have a particular field-of-view (FOV) as shown. A number of different cameras are suitable for use in the invention of this application. Excellent silicon detector staring array imagers and CCD (charge coupled device) based cameras are readily available at reasonable prices and would be suitable.

A solid state laser, Doubled Nd:YAG (Me2 C7 Mi2) emitting light at 532 nm would be ideal for use in the invention of this application. Alternatively, an argon laser, filtered to emit blue-green light, may also be used. Other sufficiently bright lasers emitting blue-green light would also be suitable for use with the present invention. In addition, conventional optical elements to collimate and expand the laser light so that it evenly illuminates a wide area are also necessary for effective spreading and penetration of the laser light.

Each camera and laser pair is preferably fitted into a watertight instrument pod 12. The instrument pods should be streamlined to avoid creating excessive drag in the water. Alternatively, if a vessel has a wide enough girth, the laser and camera pairs may be mounted directly to the hull of the ship. If the vessel is not wide enough to provide a platform for good hyperstereo separation, the instrument pods may be positioned on outriggers 62, 64, 66 and 68 extending laterally from the hull of the vessel near the bow and stern, respectively. On a surface ship, the pods should be positioned at, or near, keel depth, i.e., as deep as possible so that the laser light penetrates as deep as possible since mine hazards are most difficult to detect when they are positioned near the ocean floor. The instrument pods may be laterally moveable to adjust for optimum hyperstereo separation and may also be raised or lowered in the water.

Typical imaging and display systems operate at a 60 Hz field or 30 Hz frame rate. A 30 Hz frame rate is generally considered the minimum acceptable frame rate to avoid perceptible flicker. The lasers 8, 9, 10 and 11 and cameras 4, 5, 6 and 7 are chopped by choppers 26 and 28 at either 30 or 60 Hz rates such that laser 8 on the left side will be illuminating the surrounding water on the left side while camera 6 on the right side is viewing, and while the camera 4 on the left side and the laser 10 on the right side are blocked. If pulsed, rather than continuous wave lasers are used, a chopper 28 for the laser may, of course, be eliminated. When laser 8 is blocked camera 4 on the same side will be unblocked and laser 10 on the opposite side will be illuminating the forward terrain but camera 6 on that side will be blocked. As explained more fully below, this arrangement is used to reduce the effects of the backscatter 16 from the laser illuminating sources. The cameras 4 and 6 are outfitted with narrow bandpass filters, 52 and 54 to allow only radiation with the same wavelength as the blue-green lasers to be detected. Appropriate optical elements (not illustrated) for the desired FOV are also provided. A single laser and camera pair on each side of the vessel, equipped with appropriate wide angle optics, may replace the dual fore and aft camera and laser pairs on each side of the vessel to approximate the field of view of the dual fore and aft system. Each camera is fitted with an optical chopper or gate to selectively open and close the camera aperture. The choppers may be mechanical or electrical such as liquid crystal shutters. The optical choppers of the fore and aft cameras positioned on one side of the vessel are triggered to open synchronously with the firing of the fore and aft lasers positioned on the opposite side. As noted, the cameras may be offset from the firing of the opposite side lasers by several nanoseconds to reduce the magnitude of the backscattered radiation from the murky water closest to the vessel. If continuous wave lasers are used optical choppers must also be fitted to the lasers to permit alternate sides to selectively illuminate.

Figure 2:
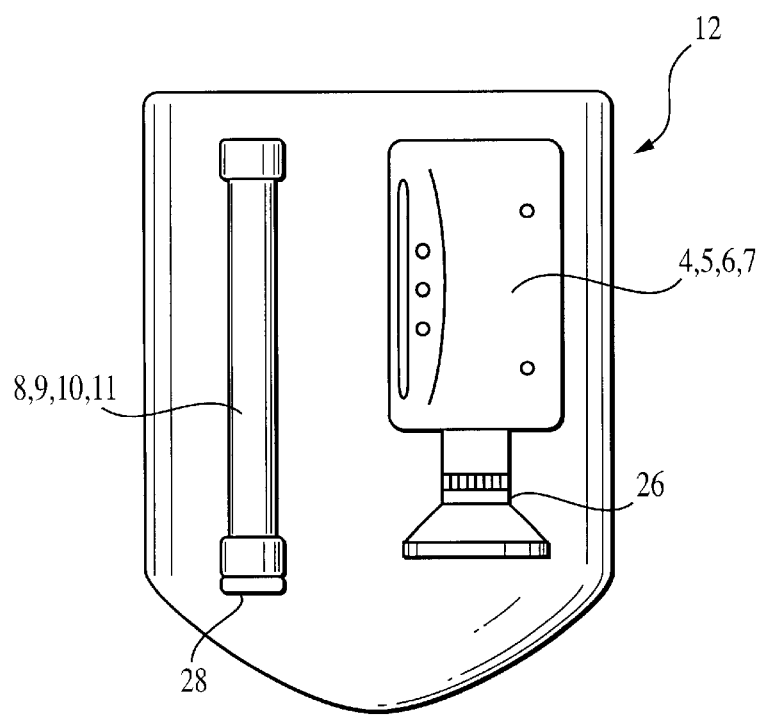
FIG. 2 depicts a schematic view of an instrument pod of the present application.
Figure 3:
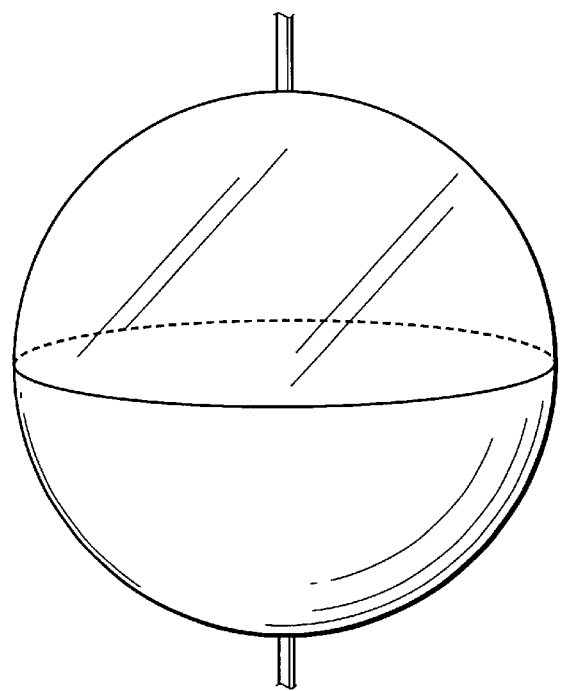
FIG. 3 depicts a spherical reflector array for towing behind a surface ship or submarine.
Figure 4:
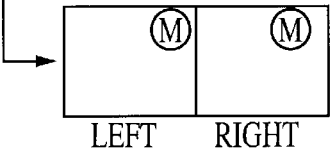
FIG. 4 shows left and right backward looking stereo images corrected for backscatter and deblurring using specular reflecting spheres.
Figure 5:
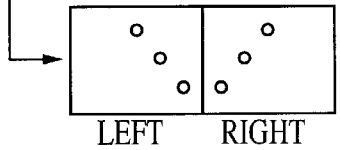
FIG. 5 shows left and right forward looking stereo images corrected for backscatter and deblurring using the results obtained from backward imagery.
Figure 6:
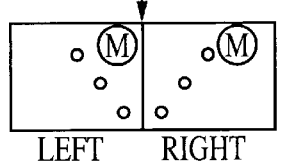
FIG. 6 shows left and right overlaid backward and forward looking imagery corrected for backscatter and blurring from which the range to object (a mine) can be derived.
Figure 7:
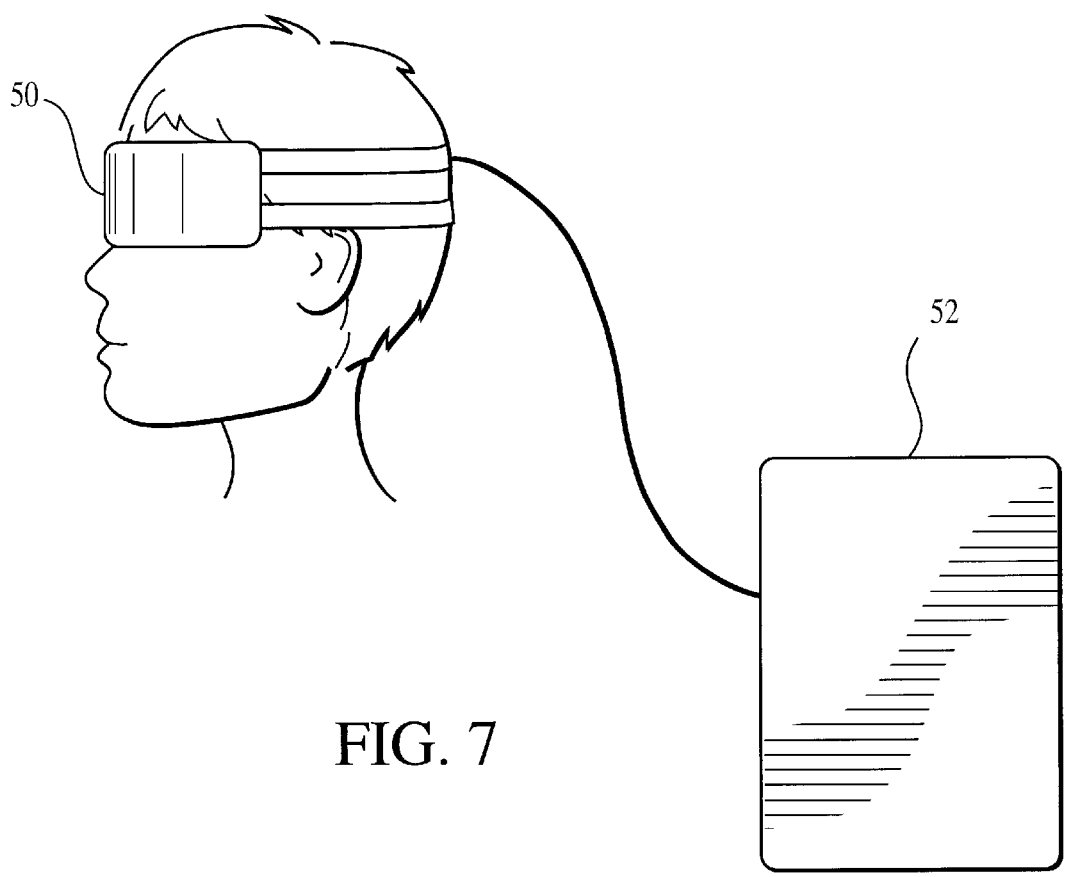
FIG. 7 shows an operator wearing a stereo headset of an image processor for viewing enhanced underwater visibility images.

In and of itself the reduction in backscattered radiation 16 by the wide baseline separation from one camera to the other is not sufficient. There must be additional mitigation mechanisms involved. In the copending application, rows of specular reflectors are placed on either side of the runway to provide sources for fusing the stereo images obtained from the port and starboard cameras. Since forward placement of reflectors is not possible for a seagoing vessel, a vessel equipped with the present invention drags a tether behind it having an array of spaced-apart, spherical specular reflectors. As shown in FIGS. 1 and 2, vessel 2 is equipped with an array of spherical specular reflection devices 30, 32, 34, 36, 38, 40, 42, 44, 46, 48 spaced along a tether 70 dragged in the water behind the vessel 2. The reflections 18, 20, 22 of the laser radiation from this pattern of reflectors will provide the mechanism necessary to use the contrast enhancement of hyperstereo vision. The individual reflectors 30, 32, 34, 36, 38, 40, 42, 44, 46, 48 will provide a small area source that will be blurred by scattering through the turbid water 14 similar to that of a street light that blurs into a halo when viewed from a distance through fog. To be able to correct for this blur the signals from the tethered line of specular reflectors 30, 32, 34, 36, 38, 40, 42, 44, 46, 48 must be increased over the background scattering radiation. To accomplish this the side-to-side scattering intensity gradient caused by the off-axis illuminating laser source is used. Because the laser is illuminating from the opposite side of the vessel 2 the scattered radiation in a given image will have more scattered radiation from the turbid water 14 on the side closest to the laser source. Thus, the left image will have more scattered radiation on its right side and the right image will have more scattered radiation on its left side. The two scattered images will however be symmetrically equal if matched cameras and lasers are used. The magnitude of the scattering pattern can be derived by comparing one image with its opposite side camera image flipping the opposite side camera image from left to right. This process is performed on both front and back image pairs using an image processing computer 52 equipped with a stereo headset 50 at the workstation of the system operator onboard the vessel 2. What is sought is a smoothed version of the backscatter produced by the laser illumination. Once a smoothed version is derived, the backscatter pattern is subtracted directly from the image that was not flipped left to right. The backscatter pattern is then flipped left to right to subtract it from the other opposite side image. The resultant images will have enhanced feature reflection radiation but will still be degraded because of scattering blur. At this point the power of the strong stereo fusion mechanism is used. The back stereo image pairs are superimposed onto the front stereo image pairs to provide enhanced spatial resolution. Thus, the operator will see a stereo image of the array of specular reflectors in his forward-looking field of view. By viewing these resultant feature images on an image processing computer with stereo headset 50 after backscatter reduction has been performed, the appropriate inverse filtering can be determined to eliminate the point spread function blurring. When the wide baseline stereo images are viewed the fusion of the two rows of specular reflectors 30, 32, 34, 36, 38, 40, 42, 44, 46, 48 will result in dramatic reduction of scene noise that does not fuse. Also reflections from background objects will be enhanced. The quality of the fusion process can be adjusted using different point spread inverse filters. Once this adjustment has been made the hyperstereo imagery will allow an enhanced view of objects in the surrounding water, greatly increasing the capability of visually identifying any underwater mine hazards in the path of vessel 2 in turbid media 14, such as seawater and greatly enhancing visibility in underwater recovery operations.

Backscattering 16 in turbid media 14 is typically at most an order of magnitude larger than the specular reflection return if the illumination is along the same line of sight as the imaging. Since the imaging is from off-axis background scatter subtraction is performed. The illuminated specular reflectors 30, 32, 34, 36, 38, 40, 42, 44, 46, 48 provide sufficient signal intensity to perform effective hyperstereo fusion and inverse point spread function deblurring.

While a preferred embodiment of the invention of this application involves the underwater detection of mine hazards and the like, and undersea exploration, generally, the concepts of hyperstereo image processing disclosed herein can be readily applied to systems for visibility enhancement and analysis of other turbid, murky media where backscattering is a problem. For instance, the present invention could be readily adapted for use in industry for detecting foreign bodies in containers of turbid or murky products where visual inspection is a problem. The invention of this application may also be used either on a surface vessel or a submarine, and may be deployed on a unmanned vessel for deep water exploration, or rescue and recovery operations.

It will be readily seen by one of ordinary skill in the art that the present invention fulfills all of the objects set forth above. After reading the foregoing specification, one of ordinary skill will be able to effect various changes, substitutions of equivalents and various other aspects of the present invention as broadly disclosed herein. It is therefore intended that the protection granted hereon be limited only by the definition contained in the appended claims and equivalents thereof.

Having thus shown and described what is at present considered to be preferred embodiments of the present invention, it should be noted that the same have been made by way of illustration and not limitation. Accordingly, all modifications, alterations and changes coming within the spirit and scope of the present invention are herein meant to be included.

What is claimed is:

1. A system to enhance visibility in a turbid, murky medium, comprising:

a first laser and a first camera mounted on the left side of a vessel and pointed forward;

a second laser and a second camera mounted on the right side of the vessel and pointed forward;

a third laser and a third camera mounted on the left side of a vessel and pointed backward;

a fourth laser and a fourth camera mounted on the right side of the vessel and pointed backward;

means for chopping the emissions from the lasers such that the first and third lasers on the left side of the vessel will be illuminating the surrounding water from the left side as the second and third cameras on the right side of the vessel are viewing the surrounding water, while the first and third cameras on the left side and the second and fourth lasers on the right side are blocked; and the second and fourth lasers on the right side of the vessel will be illuminating the surrounding water from the right side as the first and third cameras on the left side are viewing the surrounding water, while the second and fourth cameras on the right side and the first and third lasers on the left side are blocked;

the cameras being outfitted with narrow bandpass filters to allow only radiation of the same wavelength as the lasers to enter the cameras;

the vessel being equipped with a tether for dragging a plurality of spaced, specular reflection devices to provide a specular reflector pattern; and computer means for comparison of the stereo images collected from the cameras to determine and subtract from the images the magnitude of the backscatter field, and to perform inverse point spread filtering based on fusion of the specular reflector pattern to produce an enhanced visibility image for location of objects and navigation in the turbid, murky water.

2. The system of claim 1 wherein the lasers emit blue-green light and the cameras are provided with filters to block all but blue-green light.

3. The system of claim 2 wherein the blue-green lasers operate at a wavelength of 532 nm.

4. The system of claim 1 wherein the means for chopping operates at 60 Hz.

5. The system of claim 1 wherein the means for chopping operates at 30 Hz.

6. The system of claim 1 wherein the lasers are pulsed.

7. The system of claim 6 wherein the means for chopping the cameras is delayed to reduce the magnitude of the backscattered radiation from the murky water closest to the vessel.

8. An apparatus for enhancing visibility in a turbid medium, comprising:
   a left-side coherent light source emitting light into the turbid medium in a first time frame;
   a right-side coherent light source emitting light into the turbid medium in a second time frame;
   a detector having a right-side field of view for capturing a right-side image from the light emitted from the left-side coherent light source in the first time frame;
   a detector having a left-side field of view for capturing a left-side image from the light emitted from the right-side coherent light source in the second time frame;
   a plurality of spaced-apart specular reflectors positioned in the field of view of at least one of the detectors for providing spatial information;
   an image processor for producing an enhanced hyperstereo output image based on the left and right-side images, and the spatial information.

9. The apparatus of claim 8 wherein at least one of the left-side and right-side coherent light sources comprises a forward and a backward looking laser, and least one of the left-side and right-side detectors comprises a forward and a backward looking camera.

10. The apparatus of claim 8 wherein the plurality of spaced-apart specular reflectors comprise reflective spheres.

11. The apparatus of claim 8 wherein the left and right side coherent light sources and left and right side detectors are positioned on the port and starboard sides, respectively, of a vessel.

12. The apparatus of claim 11 wherein the left and right side coherent light sources and detectors are matched and comprise forward and backward looking laser and camera pairs positioned in instrument pods.

13. The apparatus of claim 12 wherein the instrument pods are positioned on outrigging.

14. The apparatus of claim 13 wherein the instrument pods are moveable to adjust for optimum hyperstereo separation.

15. The apparatus of claim 8 wherein the signal processing comprises flipping at least one image from left-to-right, subtracting the flipped image from the opposite side image.

16. The apparatus of claim 15 wherein the signal processing comprises inverse filtering to eliminate point spread function blurring.

17. A method for illuminating objects in a turbid medium comprising:
   illuminating the turbid medium in a first time frame with a left-side coherent light source;
   illuminating the turbid medium in a second time frame with a right-side coherent light source;
   capturing a right-side image from the light emitted from the left-side coherent light source in the first time frame with a detector having a right-side field of view;
   capturing a left-side image from the light emitted from the right-side coherent light source in the second time frame with a detector having a left-side filed of view;
   positioning a plurality of spaced-apart specular reflectors in the field of view of at least one of the detectors for providing spatial information;
   producing an enhanced hyperstereo output image based on the left and right-side images, and the spatial information.

18. The method of claim 17 wherein producing an enhanced hyperstereo output image comprises flipping at least one image from left-to-right and subtracting the flipped image from the opposite side image.

19. The method of claim 18 wherein producing an enhanced hyperstereo output image comprises inverse filtering to eliminate point spread function blurring.

* * * * *